United States Patent [19]

Lindaberry

[11] 4,436,719

[45] Mar. 13, 1984

[54] MICROENCAPSULATED INSECTICIDAL PERSISTENCY THROUGH THE USE OF GELATIN

[75] Inventor: Harold L. Lindaberry, Ambler, Pa.

[73] Assignee: Pennwalt Corporation, Philadelphia, Pa.

[21] Appl. No.: 391,650

[22] Filed: Jun. 24, 1982

Related U.S. Application Data

[63] Continuation of Ser. No. 241,091, Mar. 6, 1981, abandoned.

[51] Int. Cl.³ .......... A61K 9/50

[52] U.S. Cl. .......... 424/37

[58] Field of Search .......... 424/31, 37, 359, 360; 43/124, 131, 132 A, 114, 136

[56] References Cited

U.S. PATENT DOCUMENTS

| | | | |
|---|---|---|---|
| 598,583 | 2/1898 | Strong | 43/114 |
| 1,444,430 | 2/1923 | Seaton | 424/359 |
| 1,604,774 | 10/1926 | Goodwin | 424/359 |
| 1,871,949 | 8/1932 | Bottrell | 424/77 |
| 2,518,191 | 8/1950 | Searle et al. | 424/360 |
| 2,911,756 | 10/1959 | Geary | 43/114 |
| 2,916,855 | 12/1959 | Thiegs | 43/124 |
| 3,270,100 | 8/1966 | Jolkovski et al. | 264/4 |
| 3,449,856 | 6/1969 | Weaver | 43/136 |
| 3,577,515 | 5/1971 | Vandegaer | 424/32 |
| 3,791,983 | 2/1974 | Maierson | 424/77 |
| 3,959,464 | 5/1976 | DeSavigny | 424/78 |
| 4,056,610 | 11/1977 | Barber et al. | 424/32 |
| 4,086,331 | 4/1978 | Neumann | 424/45 |
| 4,107,292 | 8/1978 | Nemeth | 424/32 |
| 4,126,959 | 11/1978 | Graham | 43/136 |

FOREIGN PATENT DOCUMENTS

| | | | |
|---|---|---|---|
| 10771/33 | 6/1934 | Australia | 424/359 |
| 2207440 | 8/1973 | Fed. Rep. of Germany | |
| 2834972 | 2/1980 | Fed. Rep. of Germany | 43/114 |
| 2901314 | 7/1980 | Fed. Rep. of Germany | 43/114 |
| 55-11546 | 1/1980 | Japan | 43/132 A |
| 105478 | 4/1917 | United Kingdom | 424/359 |
| 413776 | 7/1934 | United Kingdom | 424/359 |
| 772591 | 4/1957 | United Kingdom | 424/360 |
| 2000007A | 1/1979 | United Kingdom | 43/124 |

OTHER PUBLICATIONS

Chem. Abstr. 42#5603; (1948) of Burgdorf, K., Reichsamt Wirtschaftsausbau Chem. Ber. PB 52021, 1145–1153 (1942) "Dispersing Wetting and Adhesive Materials for Plant Protection . . . " Adhesives for Spray Mixts. Include: Glue, Gelatin Casein Albumin etc.

Chem. Abstr. 94 (17):134176M Apr. 27, 1981 of Rom. Patent 67,137 Oct. 30, 1979, Cruceanu et al. "Insecticidal Compn. Wettable Powder" (Gelatin, Boneglue)

Chem. Abstr. 54:7049C (1960) at Berlin et al., 12 Vest. Vyshikh. Vcheb. Zavedenii Khim. 30 v. Tekhnol, 2:622–625 (1959).

Chem. Abstr. 30#6085 (9) (1936)#2420(2) (1936) 30#785⁹ (1936) 29#8172⁷ (1935) 21#990⁴ (1927) (19#1328¹¹(1925) 19#1064⁶(1925) 18#2264¹¹(1924).

Chem. Abstr. 75#34497f (1971) of Fogle et al., S. Afr. 70 02725 ⁰² Dec. 1970 Minute Pesticide Cont. Capsules.

Markin et al., J. Econ. Entomol 64 (1): 193–196 Feb. 1971 Markin et al. J. Econ. Entomol. 68 (5) 711–712, Oct. 1975.

Pesticide Science 4, pp. 51–57 (1973), A Comparison of Sticker Performance Against Rainwashing of Microcapsules on Leaf Surfaces, F. T. Phillips et al.

Encyclopedia of Chemical Tech., Kirk-Othmer, 2nd Ed., (1966), vol. 10, pp. 499–509.

*Primary Examiner*—Shep K. Rose

[57] ABSTRACT

Novel insecticides are disclosed having improved persistency. Association of certain type B gelatins with microencapsulated insecticides especially those employing polyamide polyurea subunits in the microcapsule walls, yields such persistency. According to a preferred embodiment, PENNCAP M, which is Pennwalt Corporation's trademark for its microencapsulated methyl parathion, is admixed with type B gelatin having average molecular weights between about 15,000 and 30,000 in a sprayable, aqueous, formulation. This formulation protects, for example, crops from insect attack for a longer period than does unmodified PENNCAP M formulations.

1 Claim, No Drawings

MICROENCAPSULATED INSECTICIDAL PERSISTENCY THROUGH THE USE OF GELATIN

This is a continuation of application Ser. No. 241,091, filed Mar. 6, 1981, abandoned.

BACKGROUND OF THE INVENTION

1. Field of the Invention

This invention relates to insecticides, to insecticidal formulations, and to processes for the protection of articles from insect attack. More particularly, this invention is directed to insecticides and the like having improved persistency or duration of protective effect. Additionally, this invention concerns such formulations and processes wherein microencapsulated insecticides are modified with type B gelatin so as to improve the adherence of such microcapsules to the articles to be protected from insects to improve persistency concomitantly.

2. Discussion of the Prior Art

Microencapsulation through an interfacial polymerization process is known. Thus, U.S. Pat. Nos. 3,270,100 issued to Jolkovski, et al and 3,577,515 issued to Vandegaer, for example, disclose interfacial polymerization techniques for the reduction of microencapsulated liquids.

U.S. Pat. No. 3,959,464 issued to DeSavigny discloses microencapsulated methyl and ethyl parathions for use as insecticides. U.S. Pat. No. 4,056,610 issued to Barber, et al, discloses microencapsulated insecticides comprising microcapsules having polyurea shells including as an integral part of the shell wall a photo-stable ultraviolet light absorbent compound.

It has been proposed to employ "stickers" with microencapsulated insecticides to improve their persistency. Thus, acrylic species have been investigated for such use. See Pesticide Science 4, pp. 51–57 (1973). Additionally, the use of non-gelatinous proteins such as casein, albumin and animal or fish glue has been proposed. It has not been suggested that improvement in persistency may be accomplished through the association of type B gelatin with microencapsulated insecticides.

OBJECTS OF THE INVENTION

It is an object of this invention to provide microencapsulated insecticides having improved persistency in the environment. A further object of the invention is to formulate improved microencapsulated insecticides which may be applied to crops in lesser quantities than unmodified microencapsulated insecticides while retaining good insecticidal effectiveness. Yet another object is to provide insect destroying procedures and processes which employ such modified microencapsulated insecticides. These and other objects are attained through the practice of one or more embodiments of the present invention.

SUMMARY OF THE INVENTION

It has been discovered that microencapsulated pesticides, especially those microencapsulated pesticides having microcapsules formed from polyamide-polyurea subunits, may be improved through the association therewith of type B gelatin having average molecular weights of from about 15,000 to about 30,000. More particularly, it has been found that the association of type B gelatin with such microencapsulated insecticides improves the persistency or temporal effectiveness in combating insect attack of such formulations. The use of type B gelatin in this context is believed to improve the persistency of the pesticide formulations through a two-fold mechanism. Such gelatin is believed to "tackify" or increase the stickiness of the microcapsules of insecticide so that they are believed to be maintained in a more substantial, longer lasting association with substrates to which they are applied. Additionally, the type B gelatin is believed to coat, at least in part, the surfaces of the microcapsules. In this way, the gelatin is believed to decrease the permeativity of the encapsulated insecticide through the capsule walls. In this way, the release of the pesticide to the environment is decreased and the persistency concomitantly increased. Type B gelatin has been shown to be effective in accomplishing this increased persistency of such microencapsulated pesticides. Additionally, the employment of type B gelatin is believed to result in persistency improvements which are greater than those obtained through the use of any tackification modifier known to the prior art. Moreover, use of type B gelatin having molecular weights of from about 15,000 to about 30,000 has been found to be preferred.

DETAILED DESCRIPTION OF THE INVENTION

According to this invention, microencapsulated insecticides are modified by associating with them amounts of type B gelatin which are effective in increasing the persistency of the insecticides. Such gelatins having an average molecular weight of from about 15,000 to about 30,000 have been found to be preferred.

Among the many insecticides which, when microencapsulated, may be associated with type B gelatin to result in insecticidal formulations having improved persistency are methyl-, and ethyl-parathion; ortho-, and meta-dichlorobenzene; malathion; carbofuran; methidathion; diazinon; fenitrithion; natural and synthetic pyrethrins and others as will occur to those skilled in the art. The only practical requirement for insecticides suitable for use in the practice of one or more embodiments of the present invention is that they be capable of use in microencapsulated form. The microencapsulation technique which is useful for the formulation of microencapsulated insecticides is best exemplified by U.S. Pat. Nos. 3,577,515 issued to Vandegaer and 3,959,464 issued to DeSavigny, both assigned to the assignee of this invention and incorporated by reference herein. As will be apparent to those skilled in the art from a perusal of the Vandegaer and DeSavigny references, there are many polymeric systems which are suitable for use in the formulation of microcapsules for insecticides. Polymeric systems which are preferred for employment in the present invention are those which employ polyamide-polyurea subunits. Preferred microencapsulated insecticides for employment with this invention are the polyamide polyurea encapsulated methyl-, and ethyl-parathions commercially distributed by the Pennwalt Corporation under the trademarks PENNCAP M and PENNCAP E.

It is known that there are, in general, two kinds of commercial gelatin, type A which is derived from acid processed collagen and type B which is derived from alkaline processed collagen. See *Encyclopedia of Chemical Technology,* Kirk-Othmer, 2nd edition, (1966), Vol. 10, pp. 499-509. Gelatin is normally a mixture of many sizes of molecules and thus may occur in average molecular weight from about 10,000 to about 250,000 with correspondingly large variations in viscosities and other properties. For the practice of the present invention, it has been found to be preferred to employ type B gelatin especially that having an average molecular weight of from about 15,000 to about 30,000. Such gelatin has a viscosity from about 10 to about 30 poises (Brookfield 26° C.). One commercial variety of such gelatin is sold by Swift Chemical Company under the tradename of "FLUID TECHNICAL PROTEIN COLLOID 2226"; this material contains a small portion of urea to improve fluidity.

The amount of gelatin employed in this invention may vary from about 0.05% to about 1.0% by volume of the total volume of insecticidal spray. While larger amounts of gelatin may be added without deleterious effect, no improvement in persistency is accompanied thereby. The gelatin-modified microencapsulated pesticides are preferably formulated as aqueous dispersions. Even more preferably, such dispersions are made to be sprayable by conventional spraying apparatus. In such formulations, the usual concentration of microencapsulated insecticide is from about 0.1% to about 30% by weight depending upon proposed mode of spray application, i.e. by tractor or by air. About 1% to about 5% by weight of insecticide is preferred. Such a dispersion may be applied to substrates to be protected, preferably commercial crops, at a rate of from about 0.25 to about 2.0 pounds of microencapsulated insecticide per acre of plants. The improved microencapsulated pesticides of this invention are conveniently prepared by suspending microencapsulated insecticide in an aqueous medium. The type B gelatin having an average molecular weight from about 15,000 to about 30,000 is then added in an amount equivalent of from about 0.05% to about 1.0% by volume of the total volume of spray. Stirring or agitation of the aqueous suspension provides the desired improved insecticide. Additional quantities of water or other fluid may be added to improve the sprayability or other physical properties of the gelatin-treated, microencapsulated insecticide. According to a preferred embodiment, a sufficiency of water is added so as to enable spraying with conventional spraying equipment.

Those skilled in the art will appreciate that the mode of application of the gelatin-modified microencapsulated insecticide according to this invention is not limited to aqueous spraying. It is also possible to apply these modified insecticides by brushing, dipping, dusting, fogging, or any other mode of insecticide application known to those skilled in the art.

The following examples are illustrative of the effectiveness of the present invention as an insecticidal spray on various types of plants and against various types of agricultural pests. Parts and percentages are by weight unless otherwise indicated. In these examples, values are presented for the percentages of pests killed when the pests are allowed to come into contact with sprayed foliage a given number of days after the occurance of the spraying. In most cases, measurement of insecticidal effectiveness is made 24, 48 and 72 hours after the insects are first contacted with the sprayed foliage. These examples should be considered to be illustrative only and are not intended to limit the scope of the invention.

EXAMPLE 1

Aqueous solutions of PENNCAP M, Pennwalt's trademark for microencapsulated methyl parathion, were applied to soybeans using a two-row tractor sprayer employing 3 T-jet 8004 nozzles and delivering 60 gallons per acre of spray. PENNCAP M was applied at a rate of 0.5 and 1.0 pounds per acre as indicated. Swift 2226, Swift's Technical Protein Colloid 2226, a type B gelatin having an average molecular weight of about 20,000, was varied as indicated as a volume percentage of the total spray. Foliage was periodically harvested and exposed to cricket populations. The crickets were checked for mortality at 24, 48 and 72 hours after exposure. The results are summarized in Table 1.

TABLE 1

| NO | PENNCAP M CONCENTRATION | SWIFT 2226 CONCENTRATION | MORTALITY | | | | | | | | |
|---|---|---|---|---|---|---|---|---|---|---|---|
| | | | 7 DAYS | | | 9 DAYS | | | 14 DAYS | | |
| | | | 24 | 48 | 72 | 24 | 48 | 72 | 24 | 48 | 72 |
| 1 | 0.5 lb/acre | 0% v/v | 20 | 57 | 73 | 9 | 16 | 32 | 0 | 11 | 12 |
| 2 | " | 0.07% v/v | 7 | 34 | 59 | 10 | 24 | 44 | 3 | 16 | 25 |
| 3 | " | 0.125% v/v | 15 | 49 | 61 | 9 | 18 | 60 | 8 | 16 | 27 |
| 4 | " | 0.025% v/v | 31 | 73 | 90 | 21 | 30 | 80 | 21 | 34 | 50 |
| 5 | 1.0 lb/acre | 0% v/v | 31 | 55 | 83 | 11 | 14 | 44 | 4 | 11 | 17 |
| 6 | " | 0.07% v/v | 20 | 47 | 67 | 14 | 23 | 53 | 2 | 4 | 15 |
| 7 | " | 0.125% v/v | 46 | 79 | 90 | 24 | 34 | 78 | 10 | 27 | 43 |
| 8 | " | 0.25% v/v | 52 | 85 | 94 | 25 | 31 | 84 | 8 | 12 | 28 |

It is apparent that greater persistency results from the inclusion of type B gelatin in PENNCAP M aqueous formulations.

EXAMPLE 2

The procedure of Example 1 was followed to assess the effectiveness of different Type B gelatins on persistency of PENNCAP M. In addition to Swift 2226 (avg. mol. wt. 20,000), Swift Technical Protein Colloids 2236 (avg. mol. wt. 40,000) and 2260 (avg. mol. wt. 80,000) were employed. (The PENNCAP M was applied at a rate of 0.5 lb/acre.) The results are summarized in Table 2. (Rain in the amount of 0.13 inches occured on the day following the spraying.)

TABLE 2

| NO | GELATIN | | MORTALITY AFTER 3 DAYS (%) | | |
|---|---|---|---|---|---|
| | | | 24 | 48 | 72 |
| 9 | None | | 3 | 16 | 32 |
| 10 | Swift 2236 | 0.05% v/v | 4 | 14 | 37 |
| 11 | Swift 2260 | 0.05% v/v | 4 | 17 | 38 |
| 12 | Swift 2226 | 0.05% v/v | 6 | 31 | 51 |

EXAMPLE 3

The procedure of Example 2 was repeated over a longer interval. PENNCAP M was applied at a rate of 1.0 lb/acre; the results are summarized in Table 3.

TABLE 3

| | | MORTALITY (%) | | | | | | | | | | | | | | | | |
|---|---|---|---|---|---|---|---|---|---|---|---|---|---|---|---|---|---|---|
| | | 5 DAYS | | | 8 DAYS | | | 10 DAYS | | | 12 DAYS | | | 14 DAYS | | | 16 DAYS | | |
| NO | GELATIN | 24 | 48 | 72 | 24 | 48 | 72 | 24 | 48 | 72 | 24 | 48 | 72 | 24 | 48 | 72 | 24 | 48 | 72 |
| 13 | None | 100 | — | — | 14 | 100 | — | 10 | — | 100 | 47 | 59 | 69 | 5 | 39 | 53 | 2 | 18 | 29 |
| 14 | Swift 2260 0.125% v/v | 100 | — | — | 38 | 100 | — | 76 | — | 100 | 42 | 60 | 87 | 6 | 46 | 52 | 1 | 4 | 13 |
| 15 | Swift 2236 0.125% v/v | 100 | — | — | 69 | 100 | — | 53 | — | 100 | 38 | 69 | 92 | 2 | 42 | 54 | 13 | 49 | 61 |
| 16 | Swift 2226 0.125% v/v | 100 | — | — | 47 | 100 | — | 62 | — | 100 | 55 | 76 | 94 | 28 | 70 | 86 | 20 | 70 | 75 |

Examples 2 and 3 demonstrate the superiority of type B gelatins having average molecular weights lower than about 30,000 as compared with those having higher average molecular weights.

What is claimed is:

1. A method for improving the persistent adherence of microcapsules of insecticide to foliage of a crop to protect said foliage from insect attack comprising:
    providing an insecticide, said insecticide being microencapsulated in microcapsules comprising polyamide-polyurea subunits;
    suspending said microencapsulated insecticide in an aqueous spray medium;
    admixing with said aqueous medium from about 0.05% to about 1.0% by volume of said medium of type B gelatin, having an average molecular weight of from about 15,000 to about 30,000 and a viscosity of from 10 to about 30 poises; and
    applying said admixture to said foliage by spraying means at a rate of from about 0.25 to about 2.0 lbs. of microencapsulated insecticide per acre of plants to improve said protection from insect attack for an improved period of time, said type B gelatin decreasing the permeactivity of the encapsulated insecticide through the capsule walls, which are coated, at least in part, and, in this way, the rate of release of the insecticide to the environment decreased, and the persistency of the insecticide concomitantly increased.

* * * * *